United States Patent
Ho et al.

(10) Patent No.: US 10,307,456 B2
(45) Date of Patent: *Jun. 4, 2019

(54) USE OF SHORT SYNTHETIC PEPTIDE FOR THE TREATMENT AND/OR PROPHYLAXIS OF DRY EYE DISEASE

(71) Applicants: Tsung-Chuan Ho, Taipei (TW); Yeou-Ping Tsao, Taipei (TW)

(72) Inventors: Tsung-Chuan Ho, Taipei (TW); Yeou-Ping Tsao, Taipei (TW)

(73) Assignee: MACKAY MEMORIAL HOSPITAL, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/552,529

(22) PCT Filed: Feb. 25, 2015

(86) PCT No.: PCT/CN2015/073257
§ 371 (c)(1),
(2) Date: Aug. 22, 2017

(87) PCT Pub. No.: WO2016/134498
PCT Pub. Date: Sep. 1, 2016

(65) Prior Publication Data
US 2018/0339010 A1    Nov. 29, 2018

(51) Int. Cl.
| C07K 7/06 | (2006.01) |
| C07K 7/00 | (2006.01) |
| C07K 14/00 | (2006.01) |
| A61K 38/00 | (2006.01) |
| A61K 38/04 | (2006.01) |
| A61K 45/00 | (2006.01) |
| A61K 45/06 | (2006.01) |
| A61K 38/16 | (2006.01) |
| A61K 38/13 | (2006.01) |
| A61K 38/14 | (2006.01) |
| A61K 31/7036 | (2006.01) |
| A61K 31/7048 | (2006.01) |
| A61K 31/7052 | (2006.01) |
| A61P 27/02 | (2006.01) |

(52) U.S. Cl.
CPC .......... *A61K 38/04* (2013.01); *A61K 31/7036* (2013.01); *A61K 31/7048* (2013.01); *A61K 31/7052* (2013.01); *A61K 38/13* (2013.01); *A61K 38/14* (2013.01); *A61K 38/16* (2013.01); *A61K 45/06* (2013.01); *A61P 27/02* (2018.01); *C07K 14/00* (2013.01); *C07K 14/001* (2013.01); *A61K 2300/00* (2013.01)

(58) Field of Classification Search
CPC ........ A61K 38/00; A61K 38/04; A61K 45/00; A61K 45/06; C07K 7/06; C07K 7/00; C07K 14/00
USPC ........................ 514/20.8, 21.7; 530/300, 329
See application file for complete search history.

(56) References Cited

U.S. PATENT DOCUMENTS 7,834,146 B2 * 11/2010 Kovalic ................. C07H 21/04
435/419

OTHER PUBLICATIONS

Hessen et al, "Dry Eye: an Inflammatory Ocular Disease," Journal of Ophthalmic and Vision Research, 2014, 9(2): 240-250.*

\* cited by examiner

*Primary Examiner* — Julie Ha

(57) ABSTRACT

Disclosed herein are synthetic peptides and compositions comprising the same for the treatment and/or prophylaxis of an ocular disease, particularly, dry eye disease. Also disclosed herein are methods of treating and/or preventing an ocular disease by administering to a subject in need of such treatment a composition containing a synthetic peptide of the present disclosure.

13 Claims, 5 Drawing Sheets

Specification includes a Sequence Listing.

SEQUENCE LISTING

<160> NUMBER OF SEQ ID NOS: 7

<210> SEQ ID NO 1
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: VARIANT
<222> LOCATION: 5..6
<223> OTHER INFORMATION: Xaa can be any amino acid

<400> SEQUENCE: 1

Asp Leu Tyr Arg Xaa Xaa Ser
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic construct

<400> SEQUENCE: 2

Asp Leu Tyr Arg Val Arg Ser
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic construct

<400> SEQUENCE: 3

Asp Leu Tyr Arg Leu Arg Ser
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic construct

<400> SEQUENCE: 4

Asp Leu Tyr Arg Gln Arg Ser
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic construct

<400> SEQUENCE: 5

Asp Leu Tyr Arg Gln Lys Ser
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic construct

```
<400> SEQUENCE: 6

Leu Tyr Arg Val Arg Ser
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic construct

<400> SEQUENCE: 7

Asp Leu Tyr Arg Val Arg
1               5
```

USE OF SHORT SYNTHETIC PEPTIDE FOR THE TREATMENT AND/OR PROPHYLAXIS OF DRY EYE DISEASE

BACKGROUND OF THE INVENTION

1. Field of the Invention

The present disclosure relates to the discovery of a short synthetic peptide, and its use for the treatment and/or prophylaxis of ocular disease.

2. Description of Related Art

Dry eye disease (DED) is a general term for a variety of conditions characterized by abnormalities in the tear film possibly resulted from damage to the corneal surface. Dry eye is characterized by symptoms such as a sandy-gritty feeling in the eye, burning, irritation, or a foreign-body sensation that worsens during the day. Patients suffering from DED complain of mild to severe symptoms, and those with severe symptoms may experience constant and disabling eye irritation, and develop ocular surface epithelial disease and sight-threatening sterile or microbial corneal ulceration. At present, the only FDA-approved prescription drugs for treating DED are corticosteroids and Restasis (0.05% cyclosporine). However, neither drug may heal damaged cornea tissue; further, both drugs take about 4-6 months to produce significant amelioration on DED symptoms or healing of the damaged corneal tissue.

Accordingly, there exists a need in the related filed of an improved medication and/or method for treating and/or preventing DED.

SUMMARY

In general, the present disclosure relates to the development of novel compounds and/or methods for treating eye disease, particular, the dry eye disease (DED).

Accordingly, the first aspect of the present disclosure aims at providing a short synthetic peptide capable of treating DED. The short synthetic peptide consisting of 7 consecutive amino acid residues set forth as DLYRX$_1$X$_2$S (SEQ ID NO: 1), wherein X$_1$ and X$_2$ are independently any amino acid residues.

According to other embodiments, X$_1$ and X$_2$ are respectively valine and arginine, and the synthetic peptide has the amino acid sequence of SEQ ID NO: 2.

According to some embodiments, X$_1$ and X$_2$ are respectively leucine and arginine, and the synthetic peptide has the amino acid sequence of SEQ ID NO: 3.

According to other embodiments, X$_1$ and X$_2$ are respectively glutamine and arginine, and the synthetic peptide has the amino acid sequence of SEQ ID NO: 4.

According to further embodiments, X$_1$ and X$_2$ are respectively glutamine and lysine, and the synthetic peptide has the amino acid sequence of SEQ ID NO: 5.

According to still further embodiments, the synthetic peptide of SEQ ID NO. 1 comprises at least one D-form amino acid residue. In some examples, the synthetic peptide of SEQ ID NO. 1 has two D-form amino acid residues.

The second aspect of the present disclosure aims to provide a method of treating a subject suffering from a dry eye disease (DED). The method comprises administering to the subject an effective amount of a synthetic peptide for ameliorating symptoms related to DED. The synthetic peptide consisting of 7 consecutive amino acid residues set forth as DLYRX$_1$X$_2$S (SEQ ID NO: 1), wherein X$_1$ and X$_2$ are independently any amino acid residues.

According to other embodiments, X$_1$ and X$_2$ are respectively valine and arginine, and the synthetic peptide has the amino acid sequence of SEQ ID NO: 2.

According to some embodiments, X$_1$ and X$_2$ are respectively leucine and arginine, and the synthetic peptide has the amino acid sequence of SEQ ID NO: 3.

According to other embodiments, X$_1$ and X$_2$ are respectively glutamine and arginine, and the synthetic peptide has the amino acid sequence of SEQ ID NO: 4.

According to further embodiments, X$_1$ and X$_2$ are respectively glutamine and lysine, and the synthetic peptide has the amino acid sequence of SEQ ID NO: 5.

According to still further embodiments, the synthetic peptide of SEQ ID NO. 1 comprises at least one D-form amino acid residue. In some examples, the synthetic peptide of SEQ ID NO. 1 has two D-form amino acid residues.

According to optional embodiments, the method may further include the step of administering to the subject an effective amount of an agent selected from the group consisting of an anti-inflammatory agent, a calcineurin inhibitor, an antibiotic, a nicotinic acetylcholine receptor agonist, and an anti-lymphangiogenic agent for treating the DED.

In some examples, the anti-inflammatory agent may be cyclosporine. The calcineurin inhibitor may be voclosporin. The antibiotic may be selected from the group consisting of, amikacin, gentamycin, kanamycin, neomycin, netilmicin, streptomycin, tobramycin, teicoplanin, vancomycin, azithromycin, clarithromycin, dirithromycin, erythromycin, roxithromycin, troleandomycin, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, sulfacetamide, sulfamethizole, sulfasalazine, sulfisoxazole, trimethoprim, cotrimoxazole, demeclocycline, doxycycline, minocycline, oxytetracycline, and tetracycline. The nicotinic acetylcholine receptor agonist may be any of pilocarpine, atropine, nicotine, epibatidine, lobeline, or imidacloprid. The anti-lymphangiogenic agent may be a vascular endothelial growth factor C (VEGF-C) antibody, a VEGF-D antibody or a VEGF-3 antibody.

In all embodiments, the subject is a human.

The third aspect of the present invention is therefore directed to the use of a synthetic peptide in the manufacture of a medicament for the treatment and/or prophylaxis of DED. The synthetic peptide consisting of 7 consecutive amino acid residues set forth as DLYRX$_1$X$_2$S (SEQ ID NO: 1), wherein X$_1$ and X$_2$ are independently any amino acid residues.

According to other embodiments, X$_1$ and X$_2$ are respectively valine and arginine, and the synthetic peptide has the amino acid sequence of SEQ ID NO: 2.

According to some embodiments, X$_1$ and X$_2$ are respectively leucine and arginine, and the synthetic peptide has the amino acid sequence of SEQ ID NO: 3.

According to other embodiments, X$_1$ and X$_2$ are respectively glutamine and arginine, and the synthetic peptide has the amino acid sequence of SEQ ID NO: 4.

According to further embodiments, X$_1$ and X$_2$ are respectively glutamine and lysine, and the synthetic peptide has the amino acid sequence of SEQ ID NO: 5.

According to still further embodiments, the synthetic peptide of SEQ ID NO. 1 comprises at least one D-form amino acid residue. In some examples, the synthetic peptide of SEQ ID NO. 1 has two D-form amino acid residues.

The details of one or more embodiments of the invention are set forth in the accompanying description below. Other features and advantages of the invention will be apparent from the detail descriptions, and from claims.

DESCRIPTION

Figure 1A:
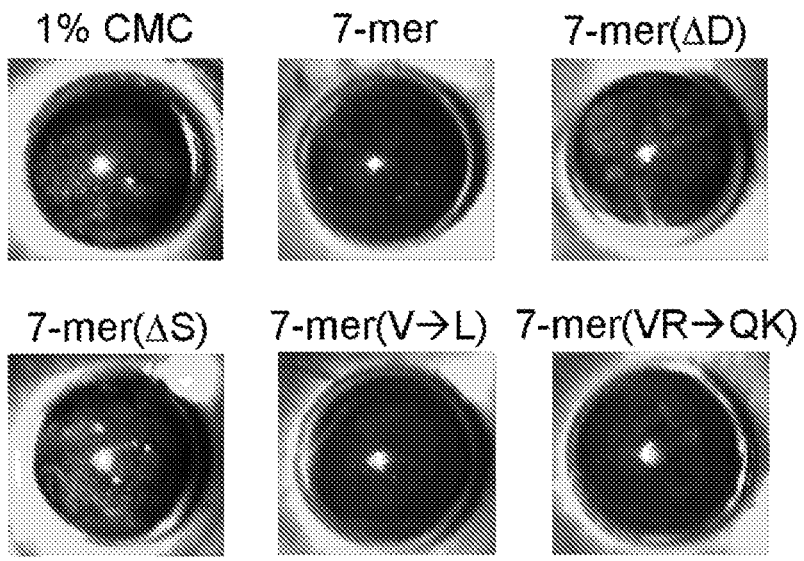
FIG. 1A are photographs of fluorescein stained corneal tissue depicting prophylactic effects of the present synthetic peptide on desiccating stressed-mice in accordance with one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

As used herein, the term "peptide" denotes a polymer of amino acid residues. By the term "synthetic peptide" as used herein, it is meant a peptide which does not comprise an entire naturally occurring protein molecule. The peptide is "synthetic" in that it may be produced by human intervention using such techniques as chemical synthesis, recombinant genetic techniques, or fragmentation of whole antigen or the like. Throughout the present disclosure, the positions of any specified amino acid residues within a peptide are numbered starting from the N terminus of the peptide.

"Percentage (%) amino acid sequence identity" with respect to the synthetic peptide sequences identified herein is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter The term "treatment" as used herein is intended to mean obtaining a desired pharmacological and/or physiologic effect, e.g., delaying, inhibiting, or ameliorating conditions associated with dry eye disease. The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered", "administering" or "administration" are used interchangeably herein to refer a mode of delivery, including, without limitation, intraveneously, intramuscularly, intraperitoneally, intraarterially, intracranially, or subcutaneously administering an agent (e.g., a compound or a composition) of the present invention.

The term "an effective amount" as used herein refers to an amount effective, at dosages, and for periods of time necessary, to achieve the desired result with respect to the treatment of a disease. For example, in the treatment of dry eye disease, an agent (i.e., a compound, a synthetic peptide, or a nucleic acid encoding a therapeutic peptide) which decrease, prevents, delays or suppresses or arrests any symptoms of the dry eye disease would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

The term "subject" or "patient" is used interchangeably herein and is intended to mean an animal including the human species that is treatable by the synthetic peptide and/or method of the present invention. The term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human.

The term "pharmaceutically acceptable carrier, excipient or stabilizer" as used herein is meant a suitable vehicle, agent or compound which is pharmaceutically acceptable for ophthalmic administration. As used herein, the term "ophthalmic composition" denotes a composition intended for application in the eye or intended for treating a device to be placed in contact with the eye, such as a contact lens.

The term "dry eye disease (DED)" as used herein is intended to mean any disorder characterized by persistent dryness of the conjunctiva and opacity of the cornea that resulted from any of the followings, decreased tear production, excessive tear evaporation, an abnormality in the production of mucus or lipids normally found in the tear layer. Causes of DED include, but are not limited to, exposure to dry environment such as airplanes and workplaces, vitamin A deficient, Sjögren's syndrome, rheumatoid arthritis and other rheumatologic diseases, chemical or thermal burns, drugs such as atenolol, chlorpheniramine, hydrochlorothiazide, isotretinoin, ketorolac, ketotifen, levocabastin, levofloxacin, oxybutynin, and tolterodine.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Detail Description of Preferred Embodiments

The present disclosure is based, at least in part, on the discovery of short synthetic peptides that are capable of treating and/or preventing a subject from developing ocular disease, such as dry eye disease (DED). Accordingly, this invention provides method and composition comprising the newly identified synthetic peptides for the treatment and/or prophylaxis of DED.

2.1 the Present Synthetic Peptides

The short synthetic peptide of the present disclosure consists of 7 consecutive amino acid residues set forth as $DLYRX_1X_2S$ (SEQ ID NO: 1), wherein $X_1$ and $X_2$ are independently any amino acid residues.

In one embodiment, $X_1$ is leucine, and $X_2$ is any amino acid residue.

In another embodiment, $X_1$ and $X_2$ are respectively valine and arginine.

In still another embodiment, $X_1$ and $X_2$ are respectively glutamine and lysine.

According to optional embodiments, the synthetic peptide of SEQ ID NO. 1 may comprise at least one D-form amino acid residue. In some examples, the synthetic peptide of SEQ ID NO. 1 has two D-form amino acid residues.

The present synthetic peptide may be synthesized in accordance with any standard peptide synthesis protocol in the art. In one embodiment, the present synthetic peptides were synthesized by use of a solid-phase peptide synthesizer (AB1433A peptide synthesizer, Applied Biosystems Inc., Life Technologies Corp., Foster City, Calif., USA) in accordance with the manufacturer's protocols. The synthetic peptides of the present disclosure are designated as 7-mer ($X_1$, $X_2$) (SEQ ID NO: 1), 7-mer (SEQ ID NO: 2), 7-mer (V→L) (SEQ ID NO: 3), 7-mer (V→Q) (SEQ ID NO: 4), and 7-mer (VR→QK) (SEQ ID NO: 5) and are described in detail in Table 1 below.

TABLE 1

The present synthetic peptides

| Peptide No. | Amino Acid Sequence | SEQ ID NO |
|---|---|---|
| 7-mer ($X_1$, $X_2$) | $NH_2$-Asp-Leu-Tyr-Arg-$X_1$-$X_2$-Ser-COOH or $DLYRX_1X_2S$ | 1 |
| 7-mer | $NH_2$-Asp-Leu-Tyr-Arg-Val-Arg-Ser-COOH or DLYRVRS | 2 |
| 7-mer (V→L) | $NH_2$-Asp-Leu-Tyr-Arg-Leu-Arg-Ser-COOH or DLYRLRS | 3 |
| 7-mer (V→Q) | $NH_2$-Asp-Leu-Tyr-Arg-Gln-Arg-Ser-COOH or DLYRQRS | 4 |
| 7-mer (VR→QK) | $NH_2$-Asp-Leu-Tyr-Arg-Gln-Lys-Ser-COOH or DLYRQKS | 5 |

$X_1$, $X_2$ are respectively any amino acid.

Any skilled person in this art may modify the synthesized peptides by methods (such as a computer simulation program) that predict the effect on polypeptide conformation of a change in polypeptide sequence, and thus may "design" or "modify" the present synthetic peptide (e.g., 7-mer) based on the information disclosed herein by proposing and testing a modified synthetic peptide to determine whether the modified synthetic peptide retains a desired function or conformation. The present synthetic peptide (e.g., 7-mer) may be modified specifically to alter a feature of the peptide unrelated to its physiological activity. For example, certain amino acids can be changed and/or deleted without affecting the physiological activity of the peptide in this study (i.e., its ability to treat DED). According to some embodiments, the fifth and sixth amino acid residues (valine and arginine, respectively) of the 7-mer can be substituted by any amino acid residues without affecting its ability to treat and/or prevent DED. This invention thus encompasses functionally equivalent derivatives of the preferred synthetic peptide of SEQ ID NO: 2 (i.e., 7-mer), including peptides having conservative amino acid substitutions.

According to other embodiments, aspartate (D) and serine (S) residues respectively located at the N- and C-terminus of SEQ ID NO: 2 are deleted, and the resulted peptides respectively designated as 7-mer-ΔD (LYRVRS, SEQ ID NO: 6) and 7-mer-ΔS (DLYRVR, SEQ ID NO: 7) do not possess any biological function towards DED. Accordingly, aspartate (D) and serine (S) residues respectively located at the N- and C-terminus of SEQ ID NO: 2 are necessary for the ability of the present synthetic peptide to treat DED, these two residues can only be substituted by conservative amino acid residues.

Alternatively, the present synthetic peptides may be prepared using recombinant technology. For example, one can clone a nucleic acid encoding the present peptide in an expression vector, in which the nucleic acid is operably linked to a regulatory sequence suitable for expressing the present peptide in a host cell. One can then introduce the vector into a suitable host cell to express the peptide. The expressed recombinant polypeptide can be purified from the host cell by methods such as ammonium sulfate precipitation and fractionation column chromatography. A peptide thus prepared can be tested for its activity according to the method described in the examples below.

The above-mentioned nucleic acids or polynucleotide can be delivered by the use of polymeric, biodegradable microparticle or microcapsule delivery devices known in the art. Another way to achieve uptake of the nucleic acid in a host is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

2.2 Compositions for the Treatment and/or Prophylaxis of DED

The present synthetic peptides are suitable for treating a subject suffering from DED or preventing a subject from developing DED.

Accordingly, a further aspect of the present disclosure is to provide a medicament comprising the present synthetic peptide for treating DED. The medicament is manufactured by mixing suitable amount of the present synthetic peptide with a pharmaceutically acceptable carrier, excipient or stabilizer into a composition suitable for ophthalmic administration, such as a lyophilized formulation or an aqueous solution. In particular embodiments, the synthetic peptide is selected from the group of peptides whose sequence is any of SEQ ID NO: 2-5, or a combination thereof.

The amount of the peptide present in the composition will depend on the peptide used. The peptide typically will be present in the composition in the amount from about 0.001% to about 10% by weight, such as 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0% by weight; in particular in an amount from about 0.01% to about 5% by weight, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0% by weight.

Pharmaceutical acceptable carriers, excipients or stabilizers for use with the synthetic peptides are well known in the relevant art, and include but are not limited to buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as ethylenediaminotetraacetic acid (EDTA); sugars such as sucrose, mannitol, trehalose or sorbitol; salt-forming counter-ions such as sodium; metal complexes (e.g., Zn-protein complexes); and/or non-ionic surfactants such as polysorbates (e.g., TWEEN®), poloxamers (e.g., PLURONICS®), or polyethylene glycol (PEG).

In a particular embodiment, the composition provided by this invention will be formulated for, and administered by, topical application. Topical formulations are generally aqueous in nature, buffered to a physiological acceptable pH and typically preserved for multi-dispensing. Thus, in a particular embodiment, the composition is a topical ophthalmic composition comprising a therapeutically effective amount of the present synthetic peptide (i.e., 7-mer, 7-mer (V→L), 7-mer (V→Q) or 7-mer (VR→QK)) and a pharmaceutically acceptable carrier for said peptide wherein the pharmaceutically acceptable carrier is a vehicle suitable for topical ophthalmic administration. As it is well-known by the skilled person in the art, various types of vehicles may be utilized. The vehicles will generally be aqueous in nature. Aqueous solutions are generally preferred, based on ease of formulation, as well as patients' ability to easily administer such compositions by means of instilling one to two drops of the solutions in the affected eyes. However, the synthetic peptide provided by the invention may also be readily incorporated into other types of compositions, such as suspensions, viscous or semi-viscous gels or other types of solid or semi-solid compositions. Suspensions may be preferred for peptides that are relatively insoluble in water. The ophthalmic compositions of the present invention may also include various other ingredients, such as buffers, preservatives, co-solvents and viscosity building agents.

In relationship to any of the compositions described herein, it is preferable that an effective amount of buffer be included to maintain the pH from about 6 to about 8, preferably about 7. Buffers used are those known to those skilled in the art, and, while not intending to be limiting, some examples are acetate, ascorbate, borate, bicarbonate, carbonate, citrate, and phosphate buffers. Preferably, the buffer comprises borate. An effective amount of buffer necessary for the purposes of this invention can be readily determined by a person skilled in the art without undue experimentation. In cases where the buffer comprises borate, it is preferable that the concentration of the borate buffer be about 0.6%.

In any of the compositions related described herein related to this invention, it is preferably to include a tonicity agent. Tonicity agents are used in ophthalmic compositions to adjust the concentration of dissolved material to the desired isotonic range. Tonicity agents are known to those skilled in the ophthalmic art, and, while not intending to be limiting, some examples include glycerin, mannitol, sorbitol, sodium chloride, and other electrolytes. Preferably, the tonicity agent is sodium chloride.

Ophthalmic formulations are typically packaged in multidose form. Preservatives are thus required to prevent microbial contamination during use. There may also be reasons to use a preservative in single use compositions depending on the individual circumstances. The term "preservative" has the meaning commonly understood in the ophthalmic art. Preservatives are used to prevent bacterial contamination in multiple-use ophthalmic preparations, and, while not intending to be limiting, examples include benzalkonium chloride, thimerosal, chlorobutanol, methyl paraben, propyl paraben, phenylethyl alcohol, edetate disodium, sorbic acid, polyquaternium-1, stabilized oxychloro complexes (otherwise known as Purite®)), phenylmercuric acetate, chlorobutanol, benzyl alcohol, or other agents known to those skilled in the art. Such preservatives are typically employed at a level of from 0.001 to 1.0 percent by weight, based on the total weight of the composition (wt %).

Under certain circumstances, a surfactant or other appropriate co-solvent might be used in any of the compositions provided by this invention which are described herein. The term "surfactant" and "co-solvent" used herein has the meaning commonly understood in the art. Surfactants are used to help solubilize the therapeutically active agent or other insoluble components of the composition, and may serve other purposes as well. Illustrative, non-limitative, examples of said compounds include polyethoxylated castor oils, Polysorbate 20, 60 and 80; Pluronic® F-68, F-84 and P-103 (BASF Corp., Parsippany N.J., USA); cyclodextrins; or other agents known to those skilled in the art. Anionic, cationic, amphoteric, zwitterionic, and non-ionic surfactants may all be used in this invention. For the purposes of this invention, it is preferable that a non-ionic surfactant, such as polysorbates, poloxamers, alcohol ethoxylates, ethylene glycol-propylene glycol block copolymers, fatty acid amides, alkylphenol ethoxylates, or phospholipids, is used in situations where it is desirable to use a surfactant. Such surfactants or co-solvents are typically employed at a level of from 0.01 to 2% by weight.

Viscosity greater than that of simple aqueous solutions may be desirable to increase ocular absorption of the active ingredient, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose or other agents known to those skilled in the art. Such agents are typically employed at a level of from 0.01 to 2 wt. %.

Another type of compound that might be used in any composition of this invention described herein is a chelating agent. The term chelating agent refers to a compound that is capable of complexing a metal, as understood by those of ordinary skill in the chemical art. Chelating agents are used in ophthalmic compositions to enhance preservative effectiveness. While not intending to be limiting, some useful chelating agents for the purposes of this invention are edetate salts, like edetate disodium, edetate calcium disodium, edetate sodium, edetate trisodium, and edetate dipotassium.

In a particular embodiment, the present synthetic peptide is administered in the form of a topical composition suitable for ophthalmic application, such as eye drops, ointments, creams, etc.

Compositions of the invention are administered topically to the eye. Depending on the type and severity of the disease, about 1 μg/kg to about 50 mg/kg (e.g., 0.1-20 mg/kg) of the present synthetic peptide is administered to the patient. A typical daily or weekly dosage might range from about 1 μg/kg to about 20 mg/kg or more. The doses utilized for any of the above-described purposes of topical administration will generally be from about 0.01 to about 100 mg per kilogram of body weight (mg/kg), administered one to several, e.g., four, six, eight or even more, times per day.

In a particular embodiment, the composition provided by the present invention comprises two or more synthetic peptides, wherein at least one of them is the 7-mer or a derivative thereof (such 7-mer (V→L), 7-mer (V→Q) or 7-mer (VR→QK) and having the capacity to treat or prevent DED. In this embodiment, the synthetic peptides can be formulated for their separate, simultaneous or successive use.

The composition provided by the invention can also be in the form of a kit. In the present invention, a "kit" is understood as a product containing the synthetic peptide(s) provided by the present invention and/or the additional therapeutic compounds forming the packaged composition such that the transport, storage and simultaneous or successive administration thereof is allowed. Therefore, the kits of the invention can contain one or more suspensions, syringes, and the like which contain the synthetic peptides of the invention and which can be prepared in a single dose or as multiple doses. The kit can additionally contain a vehicle suitable for solubilizing the synthetic peptides such as aqueous media such as saline solution, Ringer's solution, dextrose and sodium chloride; water-soluble media such as alcohol, polyethylene glycol, propylethylene glycol; and water-insoluble vehicles if necessary. Another component which may be present in the kit is a package which allows maintaining the compositions of the invention within determined limits. Materials suitable for preparing such packages include glass, plastic (polyethylene, polypropylene, polycarbonate and the like), bottles, vials, paper, sachets and the like.

The kit of the invention can additionally contain instructions for the simultaneous, successive or separate administration of the different formulations present in the kit. Therefore, the kit of the invention can further comprise instructions for the simultaneous, successive or separate administration of the different components. Said instructions can be in the form of printed material or in the form of an electronic support which can store the instructions such that they can be read by a subject, such as electronic storage media (magnetic disks, tapes and the like), optical media (CD-ROM, DVD) and the like. The media can additionally or alternatively contain Internet webpages providing said instructions.

2.3 Methods for the Treatment and/or Prophylaxis of DED

As it has been indicated above, the findings described in the present invention are useful for the prevention and/or treatment of DED.

The present invention therefore relates to a method for the prevention and/or treatment of DED, which comprises topically administering to a subject in need thereof a medicament or a composition comprising a synthetic peptide consisting of 7 consecutive amino acid residues set forth as DLYRX$_1$X$_2$S (SEQ ID NO: 1), wherein X$_1$ and X$_2$ are independently any amino acid residues; and a pharmaceutically acceptable carrier.

In a particular embodiment, the synthetic peptide is in the form of a composition, wherein the composition comprises one or more of the synthetic peptides. In particular embodiments, the synthetic peptide is selected from the group of peptides whose sequence is any of SEQ ID NO: 2-5, or a combination thereof.

Optionally, the method may further include administering to the subject an effective amount of an agent selected from the group consisting of an anti-inflammatory agent, a calcineurin inhibitor, an antibiotic, a nicotinic acetylcholine receptor agonist, and an anti-lymphangiogenic agent for treating DED.

In some examples, the anti-inflammatory agent may be cyclosporine. The calcineurin inhibitor may be voclosporin. The antibiotic may be selected from the group consisting of, amikacin, gentamycin, kanamycin, neomycin, netilmicin, streptomycin, tobramycin, teicoplanin, vancomycin, azithromycin, clarithromycin, dirithromycin, erythromycin, roxithromycin, troleandomycin, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, sulfacetamide, sulfamethizole, sulfasalazine, sulfisoxazole, trimethoprim, cotrimoxazole, demeclocycline, doxycycline, minocycline, oxytetracycline, and tetracycline. The nicotinic acetylcholine receptor agonist may be any of pilocarpine, atropine, nicotine, epibatidine, lobeline, or imidacloprid. The anti-lymphangiogenic agent may be a vascular endothelial growth factor C (VEGF-C) antibody, a VEGF-D antibody or a VEGF-3 antibody.

In all embodiments, the subject suitable for treatment is a human.

The present invention will now be described more specifically with reference to the following embodiments, which are provided for the purpose of demonstration rather than limitation.

EXAMPLES

Materials and Methods
Materials

Carboxymethylcellulose sodium (CMC), period acid Schiff (PAS) reagent and dexamethasone were all from Sigma-Aldrich (St. Louis, Mo., USA). CMC (1% w/v) in balanced salt solution was used as 7-mer vehicle. All peptides were synthesized by GenScript (Piscataway, N.J., USA), in which each peptide was modified by acetylation at the NH$_2$ terminus and amidation at the COOH terminus to improve its stability, and was subsequently characterized using mass spectrometry (>95% purity).

Experimental Animals

C57BL/6 mice (7-8 weeks old, each weighted about 18 to 25 g) were used in the present study. All mice were maintained in the animal facility in accordance with the procedures approved by Mackay Memorial Hospital Review Board (Taiwan, R.O. C.). All animal experimental procedures were conducted according to the ARVO Statement for the Use of Animals in Ophthalmic and Vision Research.

Dry Eye Animal Model

Dry eyes were induced by placing mice in a controlled environment chamber (CEC) in accordance with procedures previously described by Barabino et al (IVOS (2005) 46(8), 2766-2771). Mice placed in the CEC were exposed to a relative humidity (RH)<25%, temperature of 20 to 22° C., and airflow of 15 L/min, 12 hours per day. Control mice were kept in a normal environment (RH>50%, no air flow, temperature of 21-23° C.) for the same duration.

Corneal Fluorescein Staining

Animals were anesthetized by an intraperitoneal injection of a mixture of zoletil (6 mg/kg) and xylazine (3 mg/kg). Corneal epithelial injury was determined by staining with topical fluorescein (Fluor-I-Strip, Ayerst Laboratories, Philadelphia, Pa.). Corneal fluorescein staining was examined with a slit-lamp biomicroscope under cobalt blue light and photographed with a digital camera. Data is presented as mean±SD. The number of fluorescein staining dots were graded in the 1-mm central cornea zone of each eye, on a standardized five-point scale (0 dot, grade 0; 1-5 dots, grade 1; 6-15 dots, grade 2; 16-30 dots, grade 3; 30 dots, grade 4). One point was added to the score if there was one area of confluent staining, and two points were added for two or more areas of confluence. (Li J et al., Mole Visions 2012, 18, 317)

Measurement of Tear Production

Tear production was measured by phenol red-impregnated cotton threads (Zone-Quick; Oasis, Glendora, Calif.). The validity of this test in mice was performed in accordance with procedures previously described by Dursun et al. (IVOS (2002) 43, 632-638). The threads were held with jeweler forceps and placed in the lateral canthus for 60 seconds. The tear production expressed in millimeters of thread wet by the tear and turned red.

Corneal Epithelial Histopathology

The corneal epithelial damage was assessed as described previously (Pflugfelder et al., 2005, Am J Pathol 166, 61-71). In brief, the number of detaching apical cells was counted from a full microscope field-of vision from three separate tissue sections, by two independent masked observers, using a 20 objective. Three mice were evaluated in each treatment Period Acid Schiff (PAS) Staining of Goblet Cells After animals were euthanized, eyes were surgically excised, fixed in 10% formalin, paraffin embedded, and cut into 5-μm sections. The sections were stained with PAS (Sigma-Aldrich) reagent suitable for detecting goblet cells in the superior and inferior conjunctiva, the PAS-stained sections were then examined and photographed with a microscope equipped with a digital camera. Statistics Results were expressed as the mean±standard error of the mean (SEM). 1-way ANOVA was used for statistical comparisons. P<0.05 was considered significant.

Example 1 the Present Synthetic Peptide Prevents Desiccating Stress-Induced Dry Eye Dry eye was created in mice using a controlled environmental chamber (CEC) in accordance with procedures described in the "material and method" section. Treatment was started on the first day when the mice were housed in CEC, in which the present synthetic peptide (i.e., 7-mer, 100 μM), peptide vehicle (1% CMC), or peptides derived from 7-mer (i.e., 7-mer-ΔD, 7-mer-ΔS, 7-mer (V→L) and 7-mer (VR→QK), 100 μM) were topically administered to eyes three times daily for 14 days. The peptides 7-mer-ΔD (LYRVRS, SEQ ID NO: 6) and 7-mer-ΔS (DLYRVR, SEQ ID NO: 7) represented peptides with one amino acid residue respectively deleted from 5-end (D; Aspartic acid) and 3'-end (S; Serine) of 7-mer, and were used as negative control peptides. In addition, the effects of single and double amino-acid substitution at 7-mer that generate 7-mer (V→L) and 7-mer (VR→QK) were also used to treat dry eye.

Figure 1B:
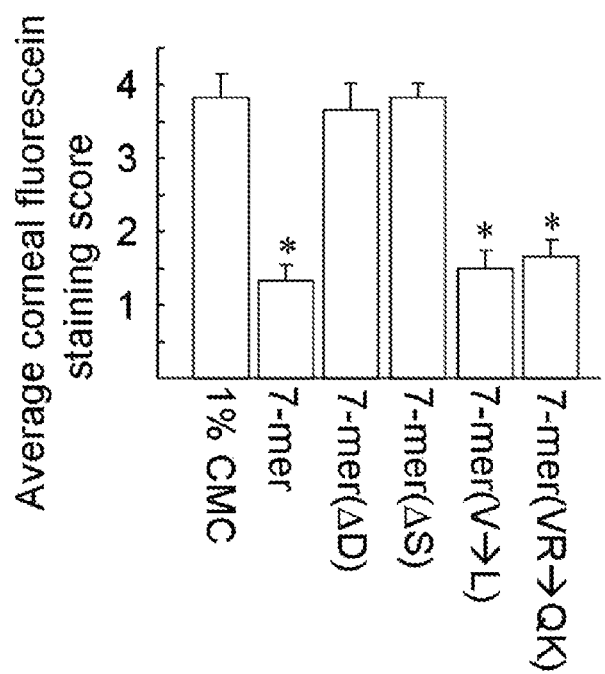
FIG. 1B is a bar graph depicting the quantitative analysis of FIG. 1A.

Fluorescein staining was used to assess changes in corneal epithelial integrity, and results are illustrated in FIGS. 1A and 1B. FIG. 1A are photographs taken on dry eyes respectively treated with the 1% CMC vehicle, 7-mer and its derivates; and FIG. 1B gives the quantitative analysis of FIG. 1A.

As evident from FIG. 1A, 1% CMC vehicle treatment did not produce prominent fluorescein staining on corneal epithelial, indicating that vehicle treatment failed to prevent desiccating stress-induced corneal epithelial damage. Conversely, significant reduction in fluorescein staining was observed in mice treated with 7-mer (3.8±0.31 versus 1.3±0.21), which indicated that the corneal epithelial structures were relatively intact in 7-mer treated mice, an indication that the 7-mer synthetic peptide was capable of protecting and/or preventing mice from developing DED. Similar protective effects were also observed in mice treated with the 7-mer derived peptides, i.e., 7-mer (V→L) and 7-mer (VR→QK); whereas the 7-mer (ΔD) and 7-mer (ΔS) had no such effect.

Figure 2:
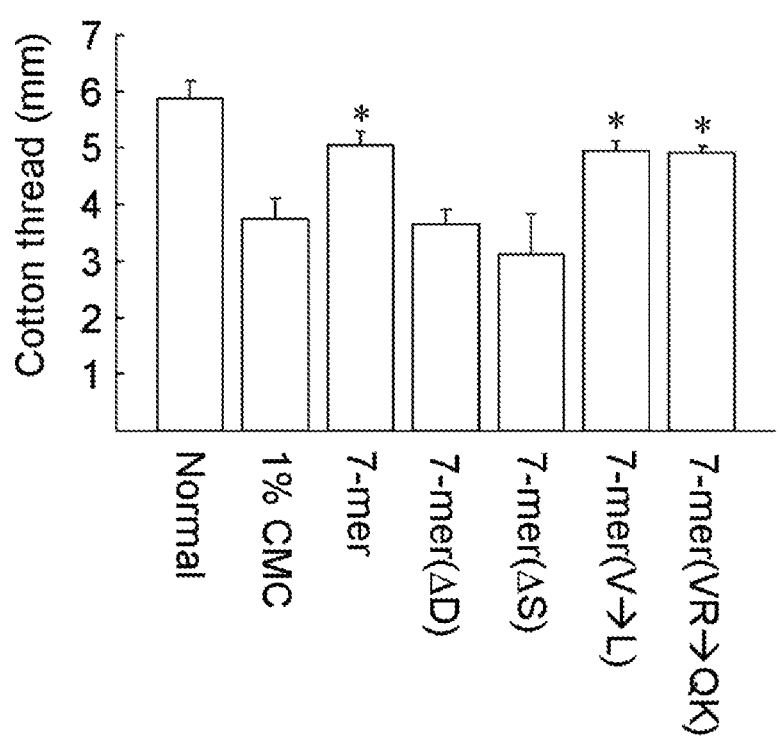
FIG. 2 illustrates the effects of the present synthetic peptide on the tear production capabilities in desiccating stressed-mice in accordance with one embodiment of the present disclosure.

The protective effects of 7-mer and its derivatives on DED were also evaluated by measuring tears produced by the test animals, and results are depicted in FIG. 2.

After housing in CEC for 14 days, tear volume produced by 1% CMC vehicle treated mice decreased significantly as compared with normal healthy mice that had not been housed in CEC or received any treatment (P<0.05). By contrast, 7-mer, 7-mer (V→L) or 7-mer (VR→QK) treatment restored the tear production capability of the mice that were subject to desiccation-stress, as compared with the vehicle control (5.1±0.21, 5.0±0.16 and 4.9±0.15 versus 3.7±0.25; FIG. 2); whereas neither 7-mer (ΔD) nor 7-mer (ΔS) peptides possessed such effect.

Results from this example confirmed that the 7-mer synthetic peptide may prevent the animal from developing desiccation-stress induced DED.

Figure 3A:
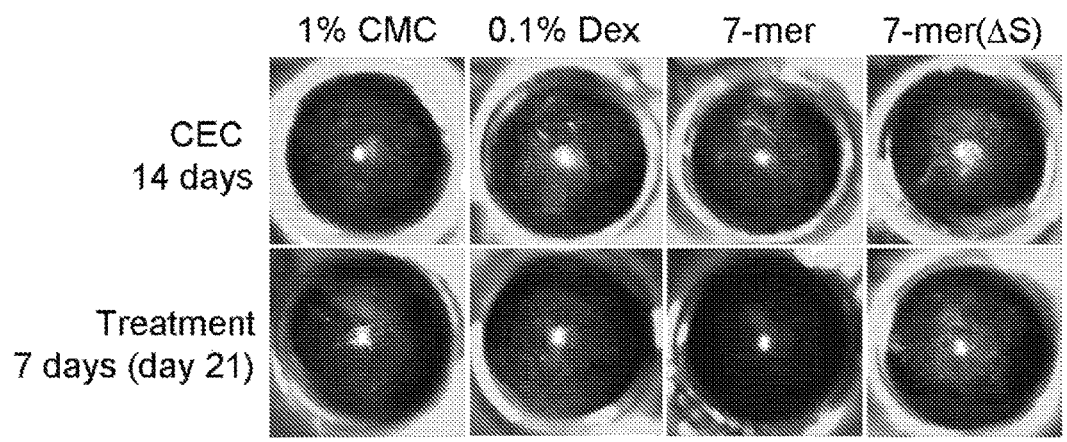
FIG. 3A are photographs of fluorescein stained corneal tissue depicting therapeutic effects of the present synthetic peptide on desiccating stressed-mice in accordance with one embodiment of the present disclosure.

Example 2 the Present Synthetic Peptide Exerts a Therapeutic Efficacy on Desiccation Stress-Induced Dry Eye Dry eye was created by housing the test animals in CEC for 14 days in accordance with procedures described in the "material and method" section. After confirmation of signs of DED by fluorescein stain (FIG. 3A; upper panel; day 14), animals were then removed from the CEC and placed in the normal environment (day 15), then started treatment by administering eye drop containing 1% CMC, 1% dexamethasone (Dex), 7-mer (100 μM), or 7-mer (ΔS) (100 μM) for 7 days (FIG. 3A; lower panel; day 21; and FIG. 3B).

Figure 3B:
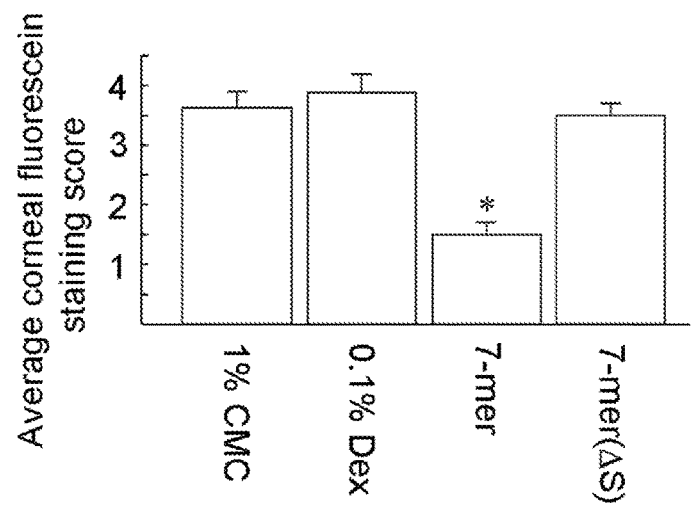
FIG. 3B is a bar graph depicting the quantitative analysis of FIG. 3A.

Quantitative results depicted in FIG. 3B indicated that 0.1% dexamethasone and the control peptide 7-mer (ΔS) had no therapeutic effect toward DED; by contrast, the 7-mer synthetic peptide of the present disclosure may significantly reduce the corneal fluorescein staining score, as compared with that of the control mice treated with 1% CMC (1.5±0.18 versus 3.6±0.26; FIG. 3B).

Figure 4A:
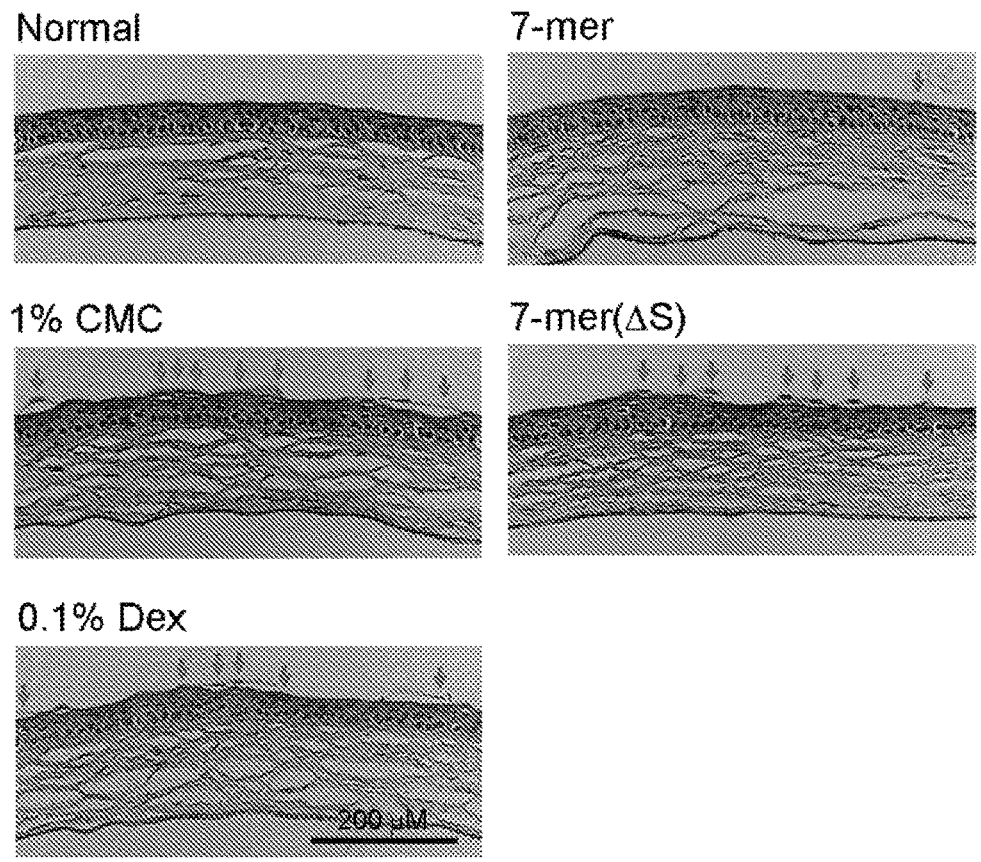
FIG. 4A are photographs illustrating histologic examination of cornea section by H&E staining in accordance with one embodiment of the present disclosure.
Figure 4B:
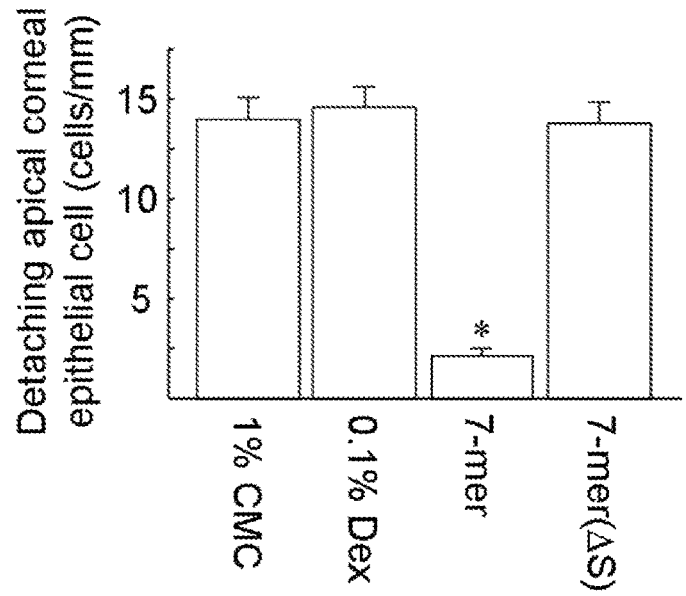
FIG. 4B is a bar graph depicting the quantitative analysis of FIG. 4A.

Detached superficial apical cells were identified on H&E stained cornea tissue sections taken from mice treated with 1% CMC vehicle, 0.1% Dex as well as the control peptide 7-mer (ΔS) (FIG. 4A), whereas no detached cells were found on cornea tissues taken from the normal healthy mice and the 7-mer treated mice. The 7-mer synthetic peptide of the present disclosure may significantly reduce the detached superficial apical cells, as compared with that of the control mice treated with 1% CMC or 7-mer (ΔS) (2.1±0.37 versus 14±1.06 and 13.8±1.03; FIG. 4B).

Figure 5A:
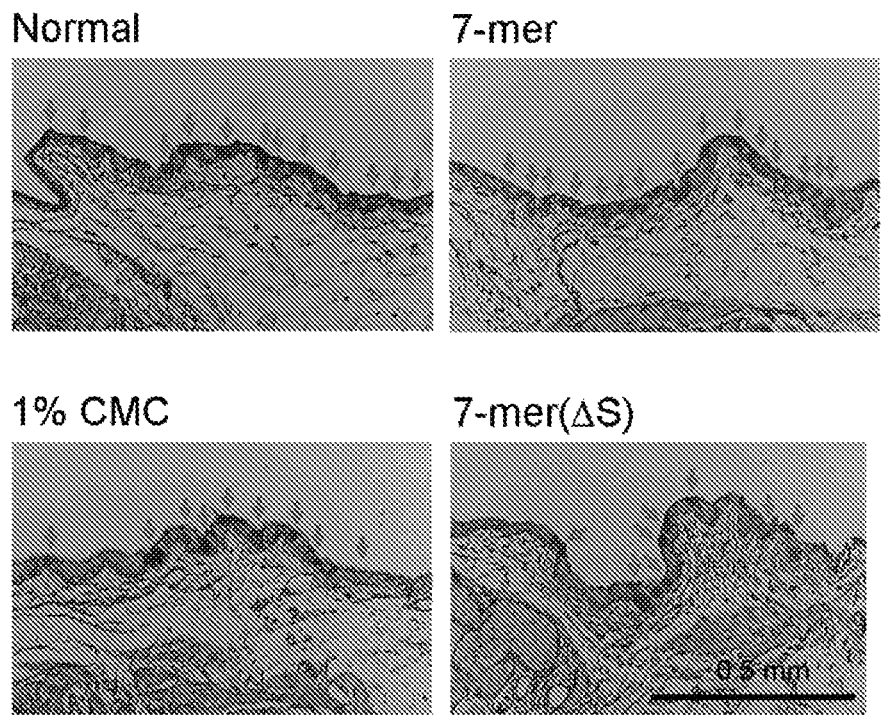
FIG. 5A are photographs of PAS-stained conjunctival epithelium in accordance with one embodiment of the present disclosure, in which goblet cells (pink, positive to PAS staining) are indicated by arrows.
Figure 5B:
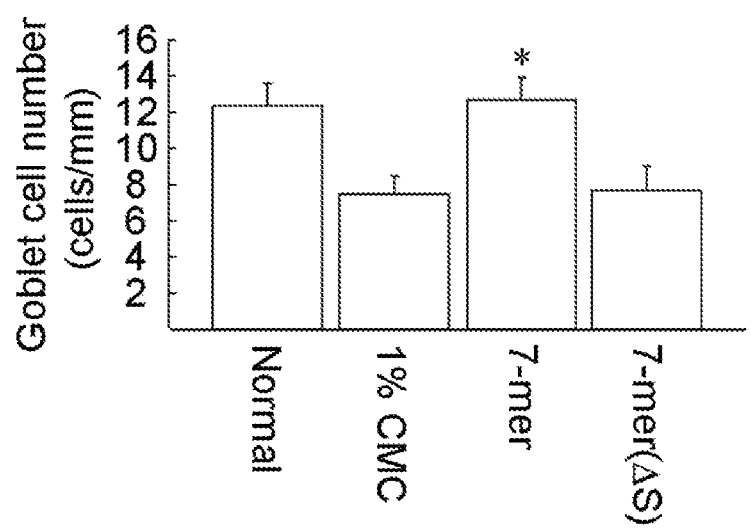
FIG. 5B a bar graph depicting the quantitative analysis of FIG. 5A.

Goblet cells are the primary cell type in epithelial responsible for the secretion of mucins, which is one of the constituent of the tear layer that help maintain corneal in a hydrated environment. PAS-stained corneal section revealed a significant reduction in the number of goblet cells in mice housed in desiccating condition for 14 days, as well as in desiccating-stressed mice treated with 1% CMC or 7-mer (ΔS) (FIG. 5A, lower panels); whereas the number of goblet cells in desiccating-stressed mice treated with the 7-mer synthetic peptide is relatively the same as that of the normal healthy mice (FIG. 5A, upper panel). The 7-mer synthetic peptide of the present disclosure may significantly induce the growth of goblet cells, as compared with that of the mice treated with 1% CMC (12.7±1.28 versus 7.5±0.96, FIG. 5B).

Taken together, the aforementioned results confirm a novel function of the short synthetic peptide of the present disclosure on the treatment and/or prophylaxis of dry eye disease.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A synthetic peptide consisting of 7 consecutive amino acid residues set forth as $DLYRX_1X_2S$ (SEQ ID NO: 1), wherein $X_1$ and $X_2$ are respectively leucine and arginine, valine and arginine, glutamine and arginine, or glutamine and lysine.

2. The synthetic peptide of claim 1, wherein at least one D-form amino acid residue is present in the amino acid sequence of SEQ ID NO: 1.

3. The synthetic peptide of claim 2, wherein at least two D-form amino acid residues are present in the amino acid sequence of SEQ ID NO: 1.

4. A method of treating a subject suffering from a dry eye disease (DED) comprising administering to the subject an effective amount of a synthetic peptide consisting of 7 consecutive amino acid residues set forth as $DLYRX_1X_2S$ (SEQ ID NO: 1), wherein $X_1$ and $X_2$ are respectively leucine and arginine, valine and arginine, glutamine and arginine, or glutamine and lysine.

5. The method of claim 4, wherein at least one D-form amino acid residue is present in the amino acid sequence of SEQ ID NO: 1.

6. The method of claim 4, further comprising administering to the subject an effective amount of an agent selected from the group consisting of an anti-inflammatory agent, a calcineurin inhibitor, an antibiotic, a nicotinic acetylcholine receptor agonist, and an anti-lymphangiogenic agent for treating the DED.

7. The method of claim 4, wherein the subject is a human.

8. The method of claim 5, wherein at least two D-form amino acid residues are present in the amino acid sequence of SEQ ID NO: 1.

9. The method of claim 6, wherein the anti-inflammatory agent is cyclosporine.

10. The method of claim 6, wherein the calcineurin inhibitor is voclosporin.

11. The method of claim 6, wherein the antibiotic is selected from the group consisting of, amikacin, gentamycin, kanamycin, neomycin, netilmicin, streptomycin, tobramycin, teicoplanin, vancomycin, azithromycin, clarithromycin, dirithromycin, erythromycin, roxithromycin, troleandomycin, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, mafenide, sulfacetamide, sulfamethizole, sulfasalazine, sulfisoxazole, trimethoprim, cotrimoxazole, demeclocycline, doxycycline, minocycline, oxytetracycline, and tetracycline.

12. The method of claim 6, wherein the nicotinic acetylcholine receptor agonist is selected from the group consisting of, pilocarpine, atropine, nicotine, epibatidine, lobeline, and imidacloprid.

13. The method of claim 6, wherein the anti-lymphangiogenic agent is a vascular endothelial growth factor C (VEGF-C) antibody, a VEGF-D antibody or a VEGF-3 antibody.

* * * * *